United States Patent [19]

Pfaffenbauer

[11] 4,139,341
[45] Feb. 13, 1979

[54] FIRING KILN, ESPECIALLY A VACUUM FIRING KILN FOR DENTAL CERAMIC PURPOSES

[75] Inventor: Ludwig Pfaffenbauer, Gschwandt, Austria

[73] Assignee: Etablissement Dentaire Ivoclar, Schaan, Liechtenstein

[21] Appl. No.: 707,131

[22] Filed: Jul. 20, 1976

[30] Foreign Application Priority Data

Jul. 31, 1975 [AT] Austria .................................. 5970/75

[51] Int. Cl.² .......................... F27B 17/00; F27B 5/04
[52] U.S. Cl. .................................... 432/184; 432/205; 432/250
[58] Field of Search ............... 432/184, 205, 206, 250, 432/5, 9, 120; 219/390; 13/20, 31, 22

[56] References Cited

U.S. PATENT DOCUMENTS

| 596,696 | 1/1898 | Custer | 219/390 X |
|---|---|---|---|
| 3,227,798 | 1/1966 | Delange et al. | 219/390 X |
| 3,800,716 | 4/1974 | Berger | 432/250 |
| 3,866,017 | 2/1975 | Keren et al. | 219/390 |
| 3,870,463 | 3/1975 | Werych | 13/22 |

FOREIGN PATENT DOCUMENTS 279937 6/1969 U.S.S.R. .................................. 432/205

Primary Examiner—John J. Camby
Attorney, Agent, or Firm—Sprung, Felfe, Horn, Lynch & Kramer

[57] ABSTRACT

A firing kiln, especially for use as a vacuum firing kiln for dental ceramic purposes, having a lower portion having a fixed firing platform, an upper portion raisable from the lower portion and in abutting relationship therewith, the lower portion having a hollow firing chamber in facing relationship with a fixed firing platform. The firing chamber includes means for emitting heat into the hollow chamber and toward the fixed firing platform, the surface of the fixed firing platform being at or above the level of the upper edge of the lower portion.

12 Claims, 2 Drawing Figures

FIRING KILN, ESPECIALLY A VACUUM FIRING KILN FOR DENTAL CERAMIC PURPOSES

BACKGROUND OF THE INVENTION

1. Field of the Invention

This invention relates to a firing kiln, especially a vacuum firing kiln for dental ceramic purposes. More especially, this invention relates to a firing kiln having a fixed firing platform and including means which automatically raise a portion of the firing kiln to allow the disposition of articles to be fired or removal of articles from the firing platform. This invention is particularly concerned with a means for slowly raising an upper portion of a firing kiln comprising a hollow firing chamber including heating means from a lower portion containing a fixed firing platform which fixed firing platform is approximately at the same height as the upper edge of the lower portion and the lower edge of the upper portion.

DISCUSSION OF THE PRIOR ART

Kilns for dental ceramic purposes have hitherto been loaded automatically, the article to be fired being placed manually on a kiln shelf or firing platform outside of the kiln, this shelf or platform then being carried in the horizontal or vertical direction into the firing chamber. The transport system increases, of course, the technical expenditure that is required, and, in the case of vertical movement of the shelf or platform, it entails an appreciable increase in structural height, and, in the case of a horizontal movement of the shelf, it entails a corresponding increase in the length and width of the kiln. The danger also exists that the article to be fired might be tipped over or shifted upon the movement of the shelf or platform, and also that the shelf or platform extended from the firing chamber will not be entirely accessible. Lastly, relatively long cool-down periods are required between firings, since the loading opening of the firing chamber is relatively small.

Kilns which are especially suitable for dental ceramic purposes are furthermore known from U.S. Pat. Nos. 569,911 and 657,202. These consist of a lower part and of an upper, raisable part hinged thereto, both parts being provided with heating means. If the upper part is raised, the article being fired remains in a recess in the lower part of the kiln, the accessibility of the article and manipulations of the article when the kiln is opened being impeded by the walls of the lower part of the kiln which at least partially surround the article being fired.

SUMMARY OF THE INVENTION

An improved firing kiln is provided, pursuant to the present invention, by a firing kiln, especially for use as a vacuum firing kiln for dental ceramic purposes, comprising a lower portion having a fixed firing platform, an upper portion raisable from said lower portion and in abutting relationship therewith, said upper portion comprising a hollow firing chamber in facing relationship to said fixed firing platform, said firing chamber comprising means for emitting heat into said chamber and towards said fixed firing platform, the surface of said fixed firing platform being at or above the level of the upper edge of said lower portion.

The invention is addressed to the problem of eliminating all these deficiencies and providing a kiln, especially a vacuum kiln, for dental ceramic purposes, having a lower part and a raisable upper part articulated thereon, which can be manufactured at lesser technical expense, has smaller dimensions, assures good accessibility to the firing platform, and requires no more than negligibly brief cool-down pauses.

The invention solves the problem in that a non-movable firing platform is located in the bottom part of the kiln and has its top surface approximately at the same level as the upper edge of the lower part or above same, and in the upper part there is provided a firing chamber having a heating means, preferably in its roof.

When the upper part is raised, the firing platform in the lower part is easily accessible, and after the article being fired has been placed on the firing platform it no longer needs to be moved, so that tipping or shifting are excluded. The expensive transport mechanism for the firing shelf or platform is superfluous, because after the article to be fired has been set in place it is necessary only to close the upper part by hand. The structural height and the other dimensions of the kiln as well are very small.

After the firing, the fired article is easily accessible when the upper part is raised, and cools down more rapidly since the heating means is located only in the upper part. The heating means can remain on while the article is being removed and while another article is being set in place, so that the time required for bringing the firing chamber back up to heat is shorter. The advantage is also obtained that, if the heating means breaks down, only the upper part need be removed or replaced.

In further development of the invention, a spring-powered cylinder which automatically raises the upper part is articulated on the upper part and lower part, so that, upon the release of the catch, the upper part rises by itself. The spring-powered cylinder can be constructed simultaneously as a hydraulic damper for the raising movement, in order to assure a slow and smooth movement.

It is especially desirable for the upper part to be held in the closed position in accordance with the invention by means of an electromagnet, because then all that need be done is to shut off the magnet energizing current in order to release the lock and bring about the automatic opening of the kiln. In this case, too, any more or less complicated locking means between the upper and lower parts of the kiln can be dispensed with.

BRIEF DESCRIPTION OF DRAWINGS

Referring to the drawings herein.

DESCRIPTION OF SPECIFIC EMBODIMENTS

Figure 1:
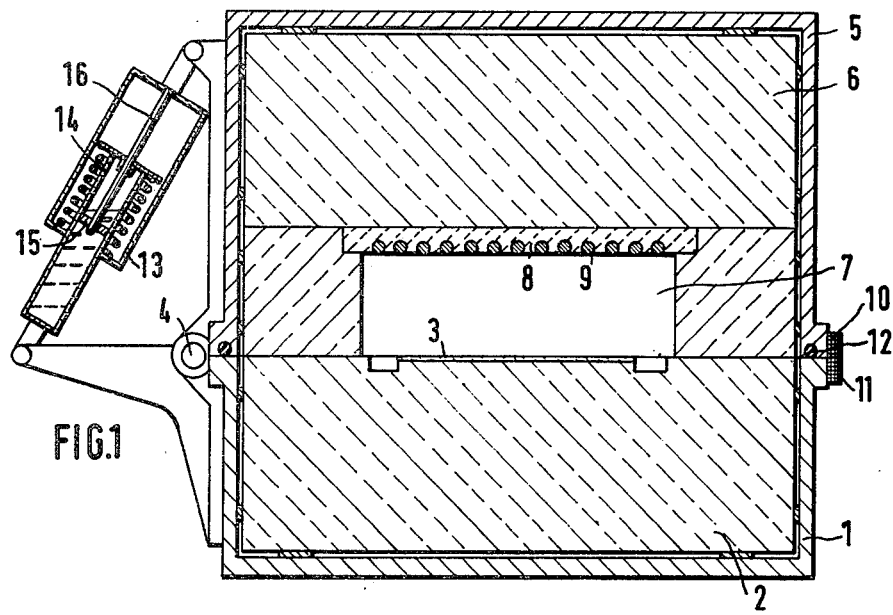
FIG. 1 is a sectional view of the kiln of the invention in closed position.
Figure 2:
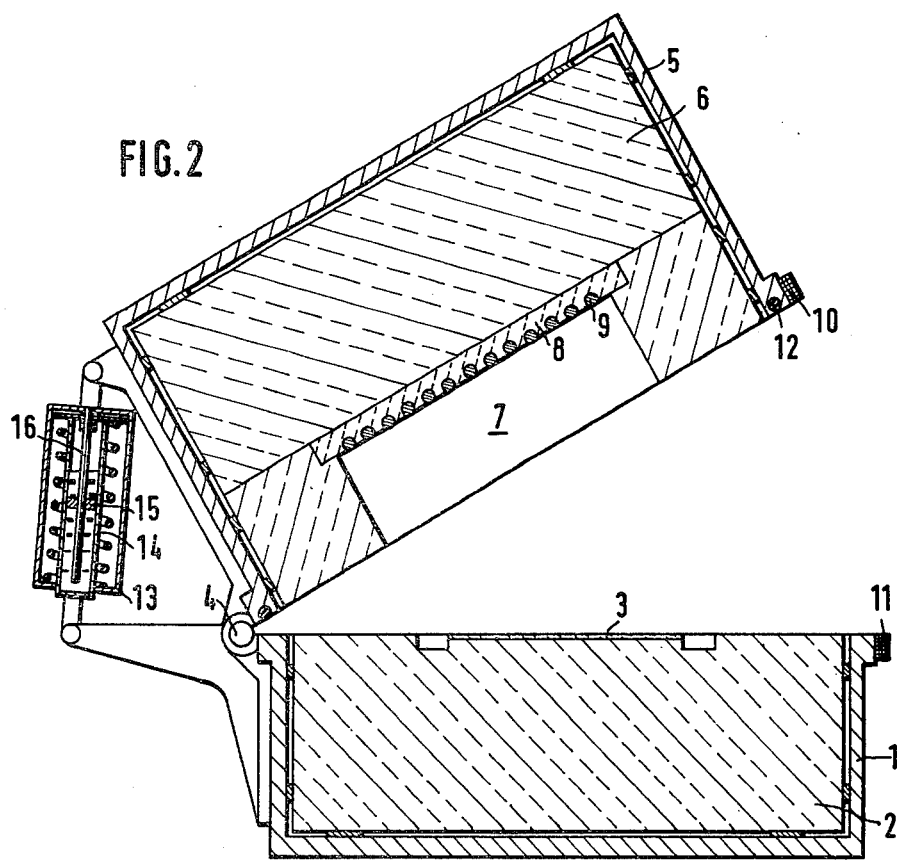
FIG. 2 is a sectional view of the kiln of the invention in open position.

The preferably cylindrical bottom part 1 of the housing is fixedly installed in the kiln rack, which is not shown, and which also contains the regulating and controlling means and the apparatus for the production, maintenance and interruption of the vacuum, and it is lined with insulating bricks 2. At the top, in the center, is the fixed firing platform 3 whose surface is disposed approximately at the height of the upper margin. The article to be fired is placed on the firing platform by hand. The surface of the platform, however, can also be slightly above the upper margin. The term "fixed firing platform", as used herein, is intended to apply also to those cases in which the firing platform is not made in one piece with the insulating brick but is mounted thereon as a separate piece. This embodiment has the advantage that the firing platform can easily be replaced with a new one if, for example, it is contaminated by dripping from a low-melting component of the article being fired.

On the bottom part 1 of the housing, an upper part 5 of the housing is articulated by means of a hinge 4. It, too, is lined with insulating bricks 6, and the firing chamber 7 is created within it. The roof of the firing chamber 7 is formed by a heating element holder 8 with the heating coils 9. An electromagnet 10-11 holds the kiln housing closed during the firing program. The seam in the housing is closed vacuum-tight by an O-ring 12.

A spring powered cylinder 13 is articulated to the upper part 5 and lower part 1. If, upon completion of the firing program, the electromagnet 10-11 is de-energized, then, when pressure equalization has been accomplished (through a duct which is not shown), the upper part 5-6 is automatically raised up by the spring powered cylinder 13. An additional cylinder 14 is contained within the spring cylinder 13 and is filled with a hydraulic fluid and divided by a piston 15 into two chambers. The piston 15 has a throttling valve which is not shown. When the upper part 5-6 swings upwardly, the rod 16, which acts as a plunger, penetrates into the lower chamber of the cylinder 14, and fluid is displaced and must pass through the throttling valve into the upper portion of cylinder 14, so that the upswinging movement is retarded. For the return movement, i.e., the closing of the kiln, the throttling valve opens wide so that the upper part of the kiln can be swung downwardly again without particularly great effort.

What is claimed is:

1. A vacuum firing kiln for dental ceramic purposes comprising a lower portion having a fixed firing platform, an upper portion hingedly connected to and raisable arcuately from said lower portion and in abutting relationship therewith, said upper portion comprising a hollow firing chamber in facing relationship to said fixed firing platform, said firing chamber comprising means for emitting heat into said chamber and toward said fixed firing platform, the surface of said fixed firing platform being at or above the level of the upper edge of said lower portion, only said upper portion containing means for emitting heat into said chamber, said kiln being provided with means for production, maintenance and interruption of vacuum, and with means retarding the upswinging movement of said upper portion.

2. A firing kiln according to claim 1 wherein said heating means is disposed on a top wall of said chamber.

3. A firing kiln according to claim 1 wherein said upper portion is articulated at an edge of said kiln to said lower portion.

4. A firing kiln according to claim 3 wherein at a side of said kiln opposite the point of articulation said upper and lower portion are secured by a catch.

5. A firing kiln according to claim 4 wherein said catch is magnetic.

6. A firing kiln according to claim 4 wherein said upper portion is connected to a spring cylinder, the spring of which is in collapsed position when said catch is engaged whereby release of said catch actuates said spring to articulate said upper portion from said lower portion and raise said upper portion.

7. A firing kiln according to claim 6 wherein said spring cylinder comprises a piston, a hydraulic cylinder, a hydraulic fluid and a reservoir in fluid communication with said cylinder through at least one port in said piston, whereby upon raising of said upper portion said piston enters said cylinder and said hydraulic fluid enters said reservoir.

8. A firing kiln according to claim 1 wherein said upper portion and lower portion are detachably secured together by an electromagnet.

9. A firing kiln according to claim 1 wherein the fixed firing platform is disposed horizontally within said lower portion.

10. A firing kiln according to claim 1 wherein substantially all of the firing chamber is disposed within said upper portion.

11. A firing kiln according to claim 3 wherein said upper portion is hingedly connected to said lower portion by a hinge disposed at approximately the same level as said firing platform.

12. A vacuum firing kiln according to claim 1 wherein said upper portion is connected to said lower portion by a hinge which is disposed approximately level with said fixed firing platform and said upper portion is articulated to said lower portion by a spring powered cylinder disposed exteriorly of said kiln and above the level of said firing platform.

* * * * *